(12) United States Patent
Han

(10) Patent No.: US 11,849,715 B1
(45) Date of Patent: Dec. 26, 2023

(54) STOVE WITH MOSQUITO REPELLENT COMPONENT

(71) Applicant: Ri Hui Han, Fujian Province (CN)

(72) Inventor: Ri Hui Han, Fujian Province (CN)

( * ) Notice: Subject to any disclaimer, the term of this patent is extended or adjusted under 35 U.S.C. 154(b) by 0 days.

(21) Appl. No.: 18/174,090

(22) Filed: Feb. 24, 2023

(30) Foreign Application Priority Data

Jan. 19, 2023 (CN) .......................... 202320150218.X

(51) Int. Cl.
*A01M 29/12* (2011.01)
*A61L 9/14* (2006.01)
*F24C 3/00* (2006.01)

(52) U.S. Cl.
CPC ............... *A01M 29/12* (2013.01); *A61L 9/14* (2013.01); *F24C 3/002* (2013.01)

(58) Field of Classification Search
CPC .......... A01M 29/12; A01M 1/205; A61L 9/14
See application file for complete search history.

(56) References Cited

U.S. PATENT DOCUMENTS

| | | | |
|---|---|---|---|
| 6,482,365 B1 * | 11/2002 | Soller | A01M 1/2066 422/126 |
| 6,503,459 B1 * | 1/2003 | Leonard | F21V 33/0004 422/126 |
| 2014/0370450 A1 * | 12/2014 | Sharma | C11C 5/006 431/288 |
| 2022/0390119 A1 * | 12/2022 | Ressler | A01M 1/2055 |

FOREIGN PATENT DOCUMENTS

| | | | |
|---|---|---|---|
| CN | 113598421 A | * | 11/2021 |
| CN | 214717845 U | * | 11/2021 |

* cited by examiner

*Primary Examiner* — Kyle A Purdy

(57) ABSTRACT

The present disclosure discloses a stove with a mosquito repellent component, the stove with a mosquito repellent component includes a stove component and a mosquito repellent component, the stove component is configured to contain fuel and allow the fuel to burn; the mosquito repellent component is provided below the stove component, the mosquito repellent component is configured to atomize mosquito repellent liquid to generate rising mosquito repellent smoke, and the bottom of the stove component blocks the mosquito repellent smoke and causes the mosquito repellent smoke to spread around along the bottom surface of the stove component. Through the arrangement of the above structure, when in use, users can use the stove component for heating, lighting and cooking, and effectively killing and driving mosquitoes around the stove and protecting users around the stove. The stove is simple in structure, convenient to use and excellent in mosquito repellent effect.

17 Claims, 9 Drawing Sheets

STOVE WITH MOSQUITO REPELLENT COMPONENT

CROSS-REFERENCE TO RELATED APPLICATIONS

The application claims priority of Chinese patent application 202320150218X, filed on 2023 Jan. 19, which is incorporated herein by reference in its entireties.

TECHNICAL FIELD

The present disclosure relates to the technical field of outdoor stoves, in particular to a stove with a mosquito repellent component.

BACKGROUND

In the fast-paced life, people increasingly expect to return to nature and relax, especially to participate in outdoor activities such as camping and picnicking. As a heating and cooking appliance, a stove has become one of the necessities for people in outdoor activities such as camping and picnicking.

However, because there are many mosquitoes outdoors, and most mosquitoes have phototaxis, people will always be bitten by mosquitoes when they use stoves for heating and cooking outdoors, so that their bodies are itchy and unbearable, greatly affecting the mood of people. Many mosquitoes carry viruses, seriously affecting the health of people. However, the existing outdoor stove products do not have the mosquito repellent function. People usually use mosquito repellent lamps, mosquito repellent incense and other products to repel mosquitoes. However, when using stoves, people usually sit around the stoves, which requires users to use a plurality of mosquito repellent devices to effectively repel mosquitoes, so that it is extremely inconvenient to use.

Therefore, the present disclosure provides a stove with a mosquito repellent component, which can effectively solve the above problems. The stove is simple in structure, convenient to use and excellent in mosquito repellent effect.

SUMMARY

In order to overcome the shortcomings of the prior art, the present disclosure provides a stove with a mosquito repellent component, which is simple in structure, convenient to use and excellent in mosquito repellent effect.

The technical solution adopted by the present disclosure to solve the technical problem is as follows:
a stove with a mosquito repellent component includes:
 a stove component, wherein the stove component is configured to contain fuel and allow the fuel to burn;
 a mosquito repellent component, wherein the mosquito repellent component is provided below the stove component, the mosquito repellent component is configured to atomize mosquito repellent liquid to generate rising mosquito repellent smoke, and the bottom of the stove component blocks the mosquito repellent smoke and causes the mosquito repellent smoke to spread around along the bottom surface of the stove component.

As the improvement of the present disclosure, the stove further includes a support arm. The lower end of the support arm is connected to the mosquito repellent component. The upper end of the support arm is connected to the stove component. A rising space is formed between the bottom of the stove component and the upper part of the mosquito repellent component. The rising space is configured to allow mosquito repellent smoke to rise and to be used. As the improvement of the present disclosure, the top of the support arm is provided with a shaft hole. The top of the stove component is provided with a rotating shaft. The rotating shaft is rotatably connected to the shaft hole. When the stove component is in working state, the stove component abuts against the support arm. As the improvement of the present disclosure, one side of the support arm facing the stove component is provided with an abutting surface. When the stove component is in working state, the stove component abuts against the abutting surface, and the shape of the abutting surface matches the shape of the outer surface of the stove component. As the improvement of the present disclosure, the stove component is provided with a locking member. The locking member rotatably protrudes from the surface of the stove component. The surface of the support arm is provided with a limiting hole. The shape of the limiting hole matches the shape of the locking member. When the locking member rotates to the unlocking position, the locking member penetrates into the limiting hole; and when the locking member rotates to the locking position, the locking member abuts against the surface of the support arm. As the improvement of the present disclosure, the stove further includes a fuel tank. An accommodating space is provided in the stove component, and the fuel tank is detachably provided in the accommodating space. As the improvement of the present disclosure, the stove component includes a bottom cover, and the bottom cover is detachably connected to the bottom of the stove component and covers the accommodating space. As the improvement of the present disclosure, the stove further includes a gas stove component. The gas stove component is provided in the accommodating space. The gas stove component is provided with a gas inlet, and the gas inlet is communicated with the tank opening of the fuel tank. As the improvement of the present disclosure, the gas stove component is provided with a gas guide channel. The gas inlet is provided at one end of the gas guide channel, and the other end of the gas guide channel is provided with a gas outlet. The gas outlet penetrates out of the accommodating space. As the improvement of the present disclosure, the gas stove component is provided with a pressure reducing valve, and the pressure reducing valve is communicated with the gas guide channel. As the improvement of the present disclosure, the stove further includes a fire distributor. The fire distributor is provided at the top of the stove component. The surface of the fire distributor is provided with a fire outlet, and the fire outlet is communicated with the gas outlet. As the improvement of the present disclosure, the top of the stove component is provided with an accommodating groove which is sunken downwards. The fire distributor is provided in the accommodating groove, and the depth of the accommodating groove matches the height of the fire distributor. As the improvement of the present disclosure, the stove further includes an adjusting knob. The gas stove component is further provided with an adjusting device. The adjusting device is configured to adjust the flow rate of combustible gas flowing through the gas guide channel. The adjusting rod of the adjusting knob is connected to the adjusting device through the side wall of the stove component, and the adjusting knob is configured to adjust the adjusting device. As the improvement of the present disclosure, the mosquito repellent component includes a shell, an ultrasonic atomizer and a cover. The upper surface of the shell is sunken downwards to form an installation groove. The ultrasonic atomizer is detachably provided in the installation groove. The cover is provided with a smoke outlet. The cover covers the installation groove. The smoke outlet corresponds to the ultrasonic atomizer. As the improvement of the present disclosure, the ultrasonic atomizer includes an ultrasonic atomizing module, a sponge rod and a mosquito repellent liquid container. The mosquito repellent liquid container is configured to contain mosquito repellent liquid. The ultrasonic atomizing module is provided at the bottle opening of the mosquito repellent liquid container. The sponge rod is connected to the ultrasonic atomizing module. The sponge rod is inserted into the mosquito repellent liquid container, and at least part of the sponge rod is immersed in the mosquito repellent liquid. As the improvement of the present disclosure, the ultrasonic atomizer further includes a battery, and the battery is electrically connected to the ultrasonic atomizing module. As the improvement of the present disclosure, the surface of the shell is provided with a slot. A hand-held part protrudes from the edge of the cover. When the cover covers the installation groove, the hand-held part is inserted into the slot. As the improvement of the present disclosure, the mosquito repellent component further includes a counterweight. The shell is provided with an accommodating cavity. The counterweight is provided at the bottom of the accommodating cavity.

As the improvement of the present disclosure, a stove with a mosquito repellent component, further includes a stove component configured to contain fuel and allow the fuel to burn; a mosquito repellent component is provided below the stove component, the mosquito repellent component configured to atomize mosquito repellent liquid to generate rising mosquito repellent smoke, and a bottom surface of the stove component configured to block the mosquito repellent smoke and causes the mosquito repellent smoke to spread around along the bottom surface of the stove component.

As the improvement of the present disclosure, the lower end of the support arm is connected to the mosquito repellent component, the upper end of the support arm is connected to the stove component, a rising space is formed between the bottom surface of the stove component and the upper part of the mosquito repellent component, and the rising space is configured to allow mosquito repellent smoke to rise and to be used.

As the improvement of the present disclosure, the top of the support arm is provided with a shaft hole, the top of the stove component is provided with a rotating shaft, the rotating shaft is rotatably connected to the shaft hole, and when the stove component is in working state, the stove component abuts against the support arm.

As the improvement of the present disclosure, the stove component is provided with a locking member, the locking member rotatably protrudes from the surface of the stove component, the surface of the support arm is provided with a limiting hole, the shape of the limiting hole matches the shape of the locking member, when the locking member rotates to the unlocking position, the locking member penetrates into the limiting hole; and when the locking member rotates to the locking position, the locking member abuts against the surface of the support arm.

As the improvement of the present disclosure, an accommodating space is provided in the stove component, and the fuel tank is detachably provided in the accommodating space.

As the improvement of the present disclosure, the stove component includes a bottom cover, and the bottom cover is detachably connected to the stove component and covers the accommodating space.

As the improvement of the present disclosure, the mosquito repellent component includes a shell, an ultrasonic atomizer and a cover, the upper surface of the shell is sunken downwards to form an installation groove, the ultrasonic atomizer is detachably provided in the installation groove, the cover is provided with a smoke outlet, the cover covers the installation groove, and the smoke outlet corresponds to the ultrasonic atomizer.

As the improvement of the present disclosure, the ultrasonic atomizer includes an ultrasonic atomizing module, a sponge rod and a mosquito repellent liquid container, the mosquito repellent liquid container is configured to contain mosquito repellent liquid, the ultrasonic atomizing module is provided at the bottle opening of the mosquito repellent liquid container, the sponge rod is connected to the ultrasonic atomizing module, the sponge rod is inserted into the mosquito repellent liquid container, and at least part of the sponge rod is immersed in the mosquito repellent liquid.

As the improvement of the present disclosure, the surface of the shell is provided with a slot, a hand-held part protrudes from the edge of the cover, and when the cover covers the installation groove, the hand-held part is inserted into the slot.

As the improvement of the present disclosure, the mosquito repellent component further includes a counterweight, the shell is provided with an accommodating cavity, and the counterweight is provided at the accommodating cavity.

The present disclosure has the following beneficial effect. Through the arrangement of the above structure, when in use, the stove component contains fuel and allows the fuel to burn, so that users can use the stove component for heating, lighting and cooking. A mosquito repellent component atomizes mosquito repellent liquid. Mosquito repellent smoke drifts upward. When meeting the bottom of the stove component, the smoke spreads around along the bottom surface of the stove component, so that the mosquito repellent smoke effectively diffuses around the stove, thereby effectively killing and driving mosquitoes around the stove and protecting users around the stove. The stove is simple in structure, convenient to use and excellent in mosquito repellent effect.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

The present disclosure is further described below in detail in combination with the accompanying drawings and embodiments.

DETAILED DESCRIPTION OF THE EMBODIMENTS

Figure 1:
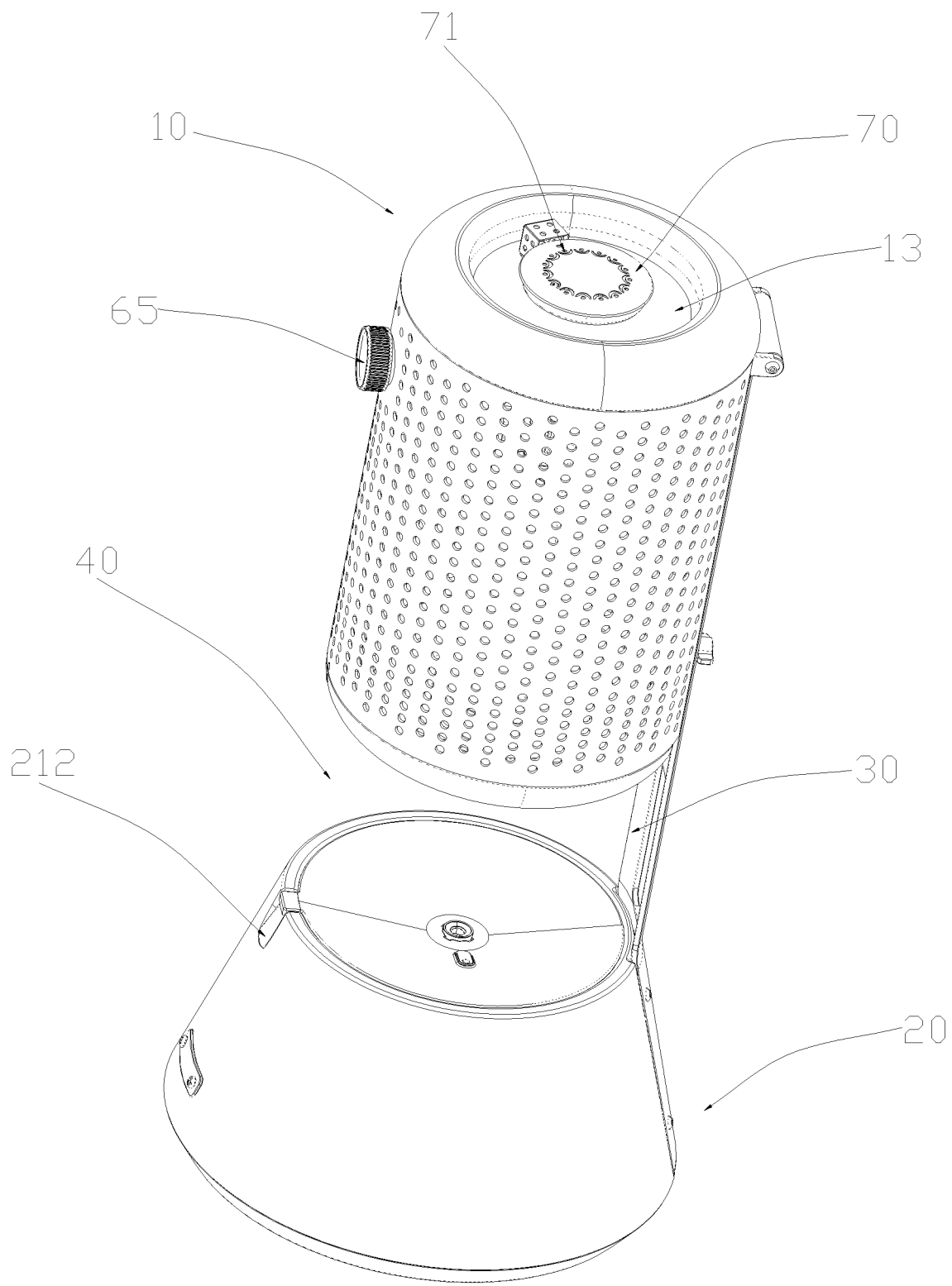
FIG. 1 is a schematic diagram of the overall structure of a stove according to the present disclosure.
Figure 2:
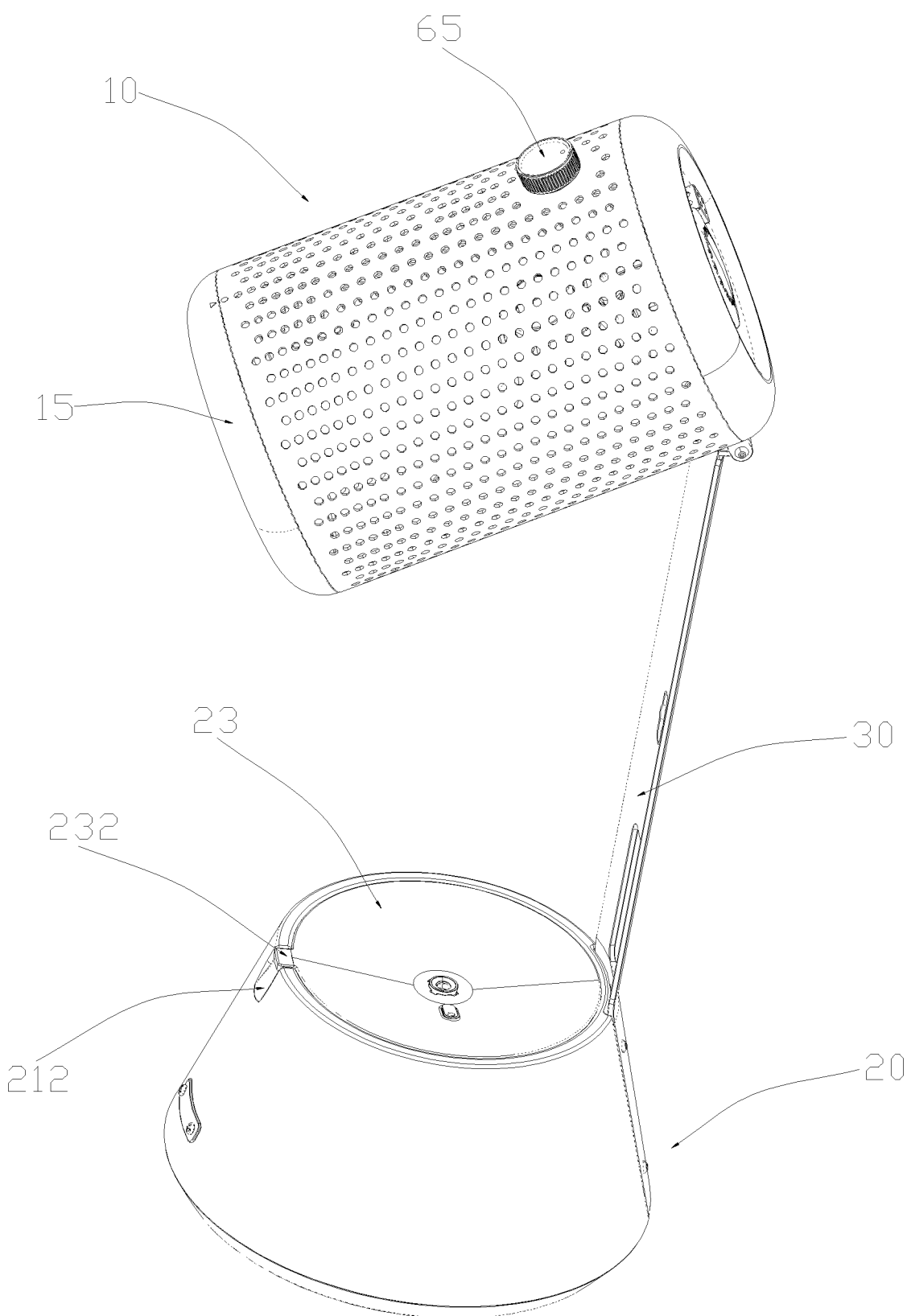
FIG. 2 is a schematic diagram of the rotating state of a stove component of a stove according to the present disclosure.
Figure 3:
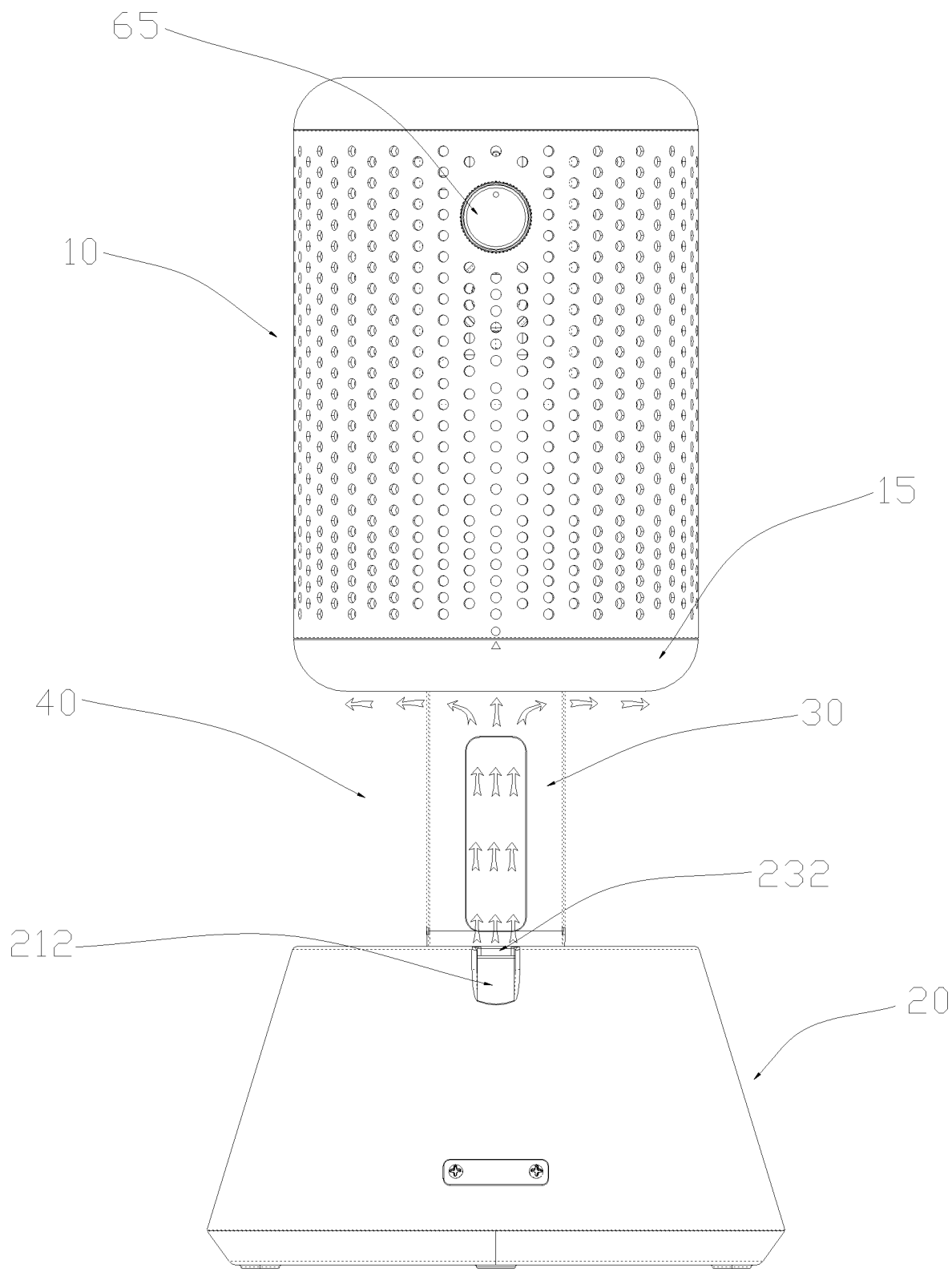
FIG. 3 is a schematic diagram of flow of mosquito repellent smoke of a stove according to the present disclosure.
Figure 4:
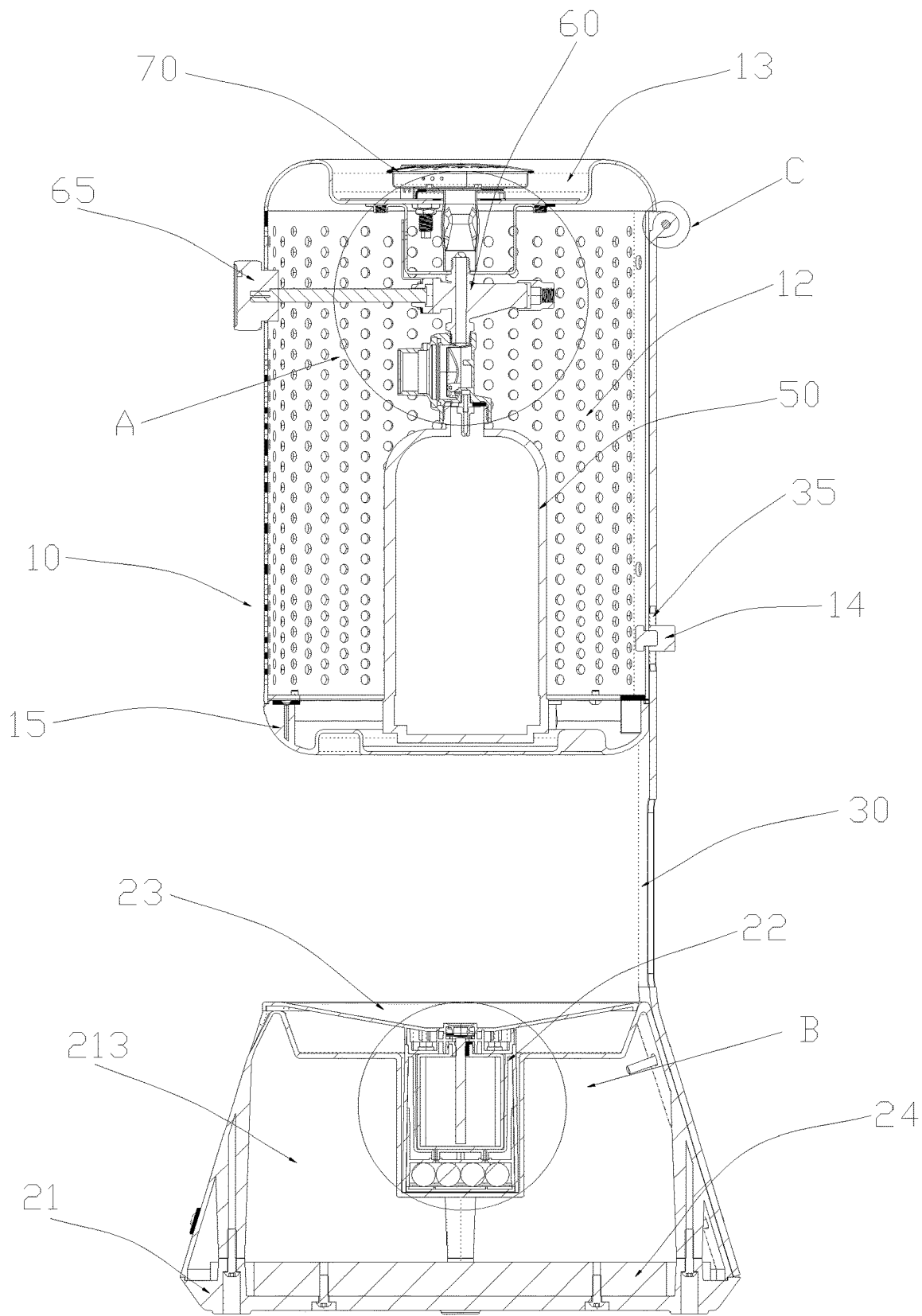
FIG. 4 is a cross-sectional view of a stove according to the present disclosure.
Figure 5:
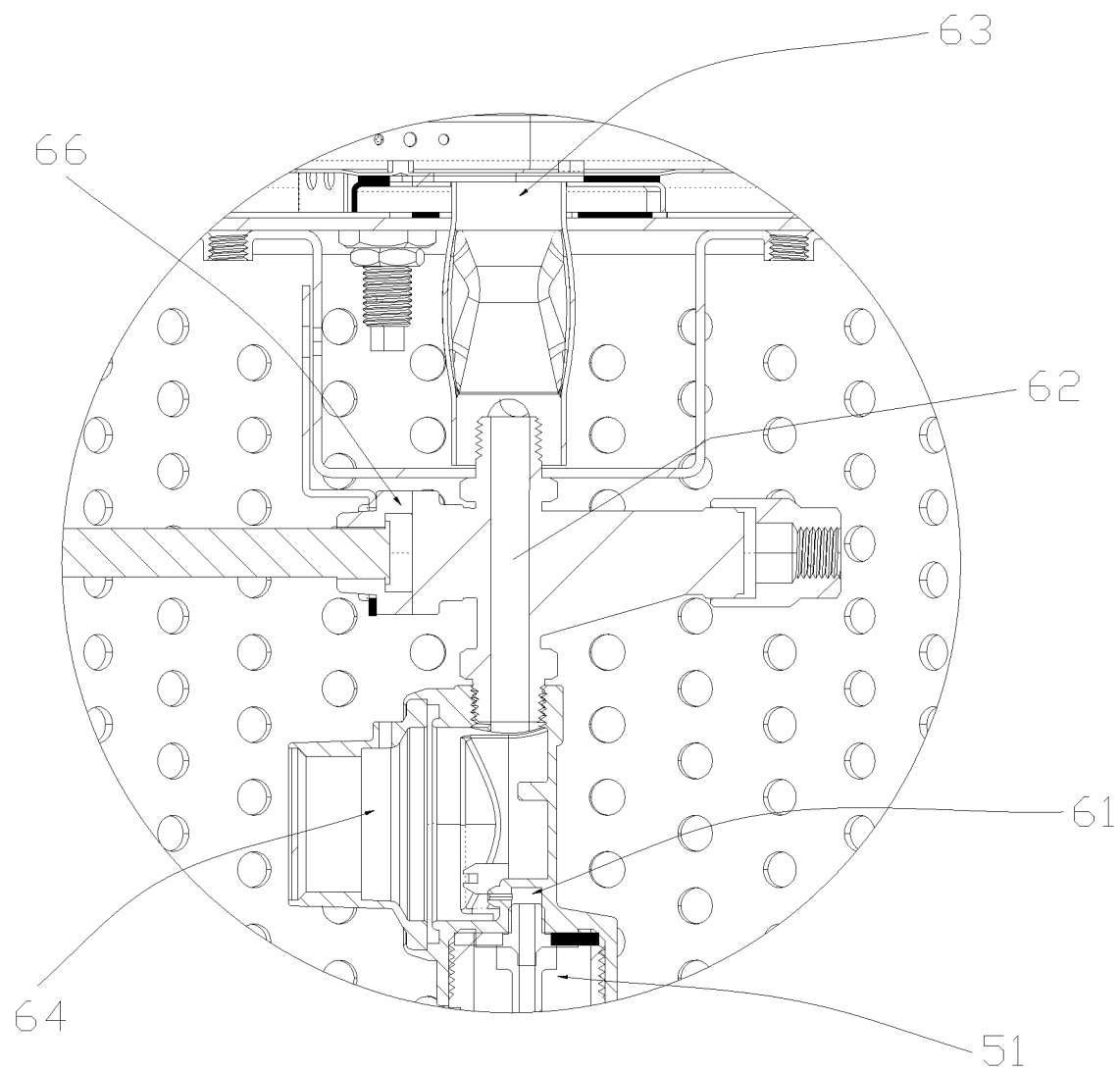
FIG. 5 is an enlarged view at circle A in FIG. 4.
Figure 6:
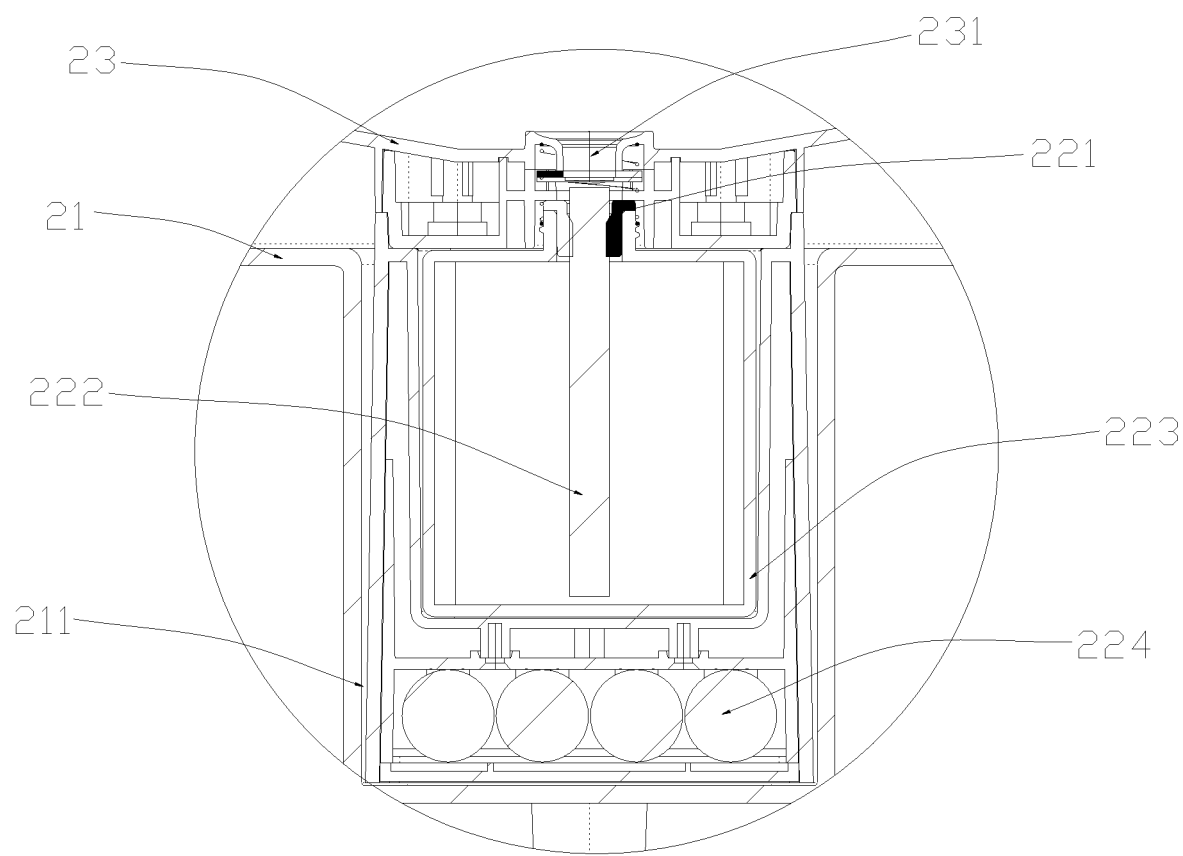
FIG. 6 is an enlarged view at circle B in FIG. 4.
Figure 7:
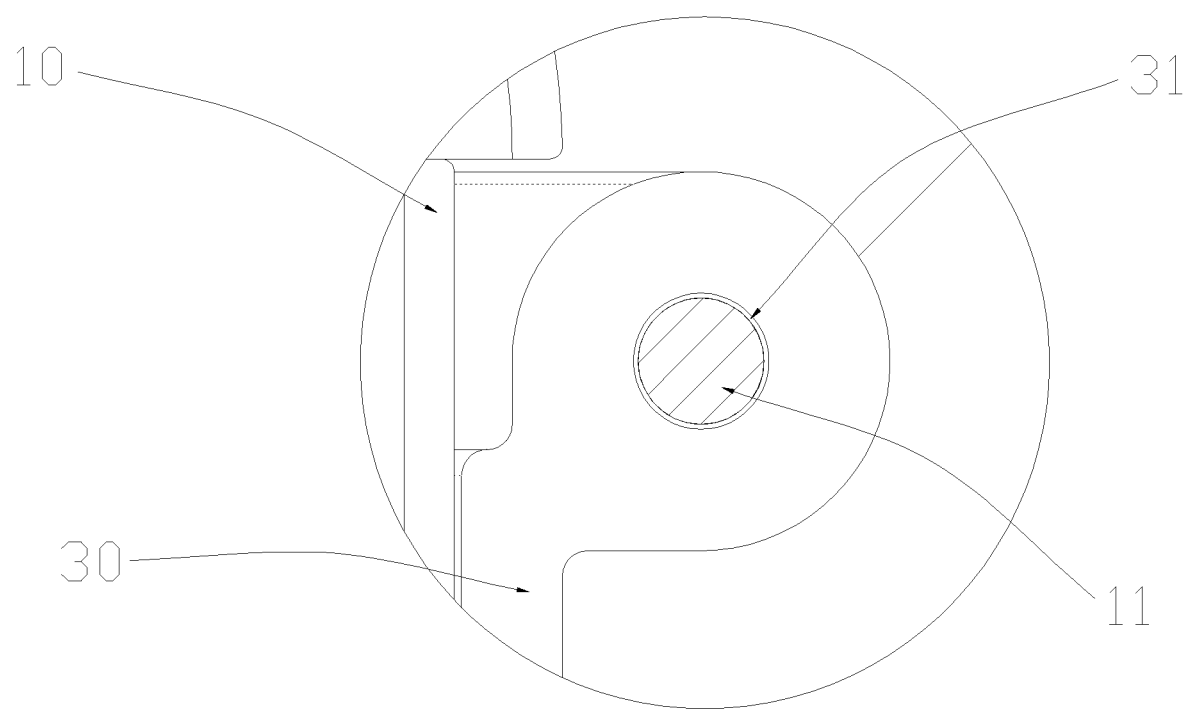
FIG. 7 is an enlarged view at circle C in FIG. 4.
Figure 8:
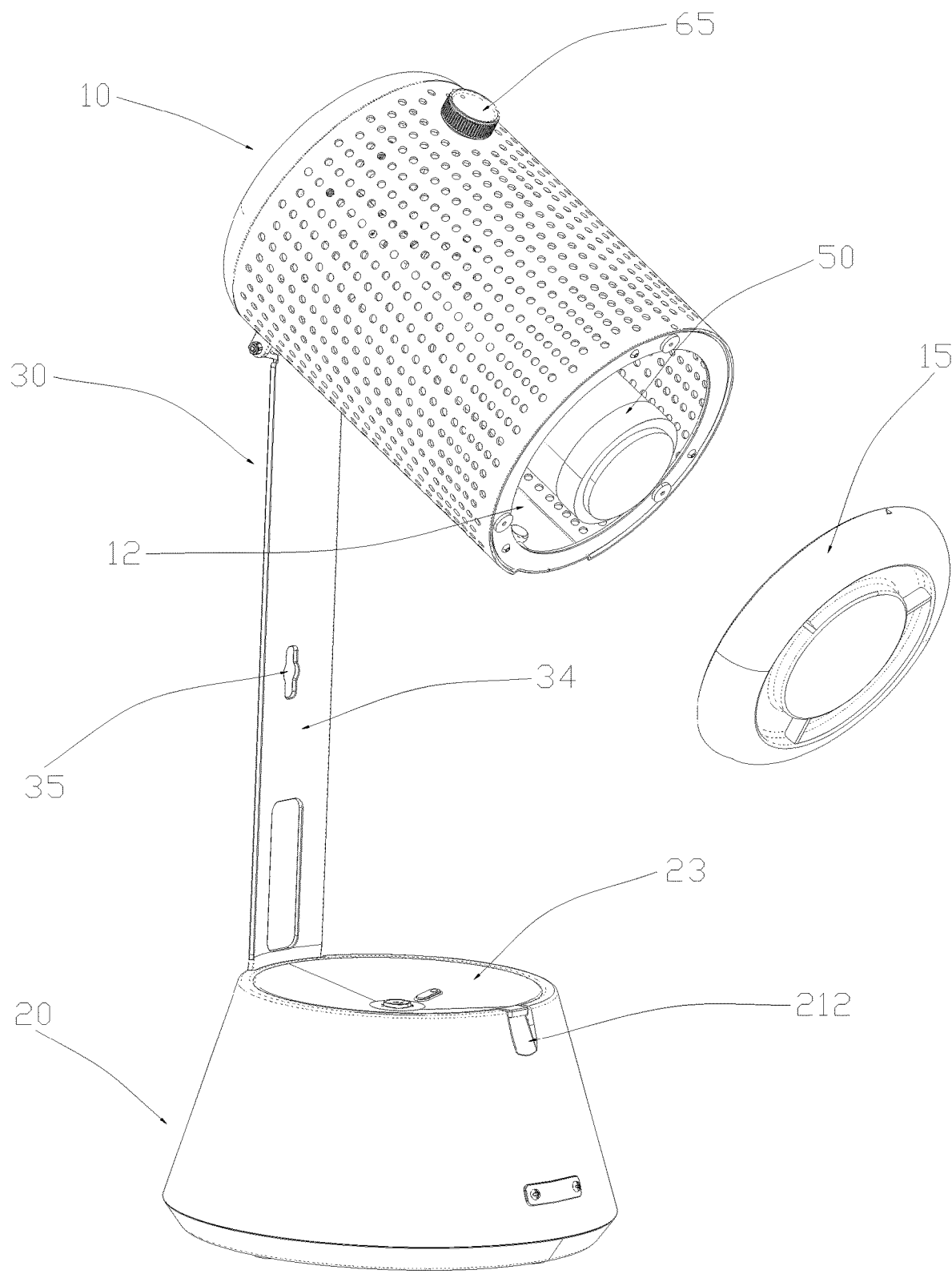
FIG. 8 is a state diagram of replacing a fuel tank of a stove according to the present disclosure.
Figure 9:
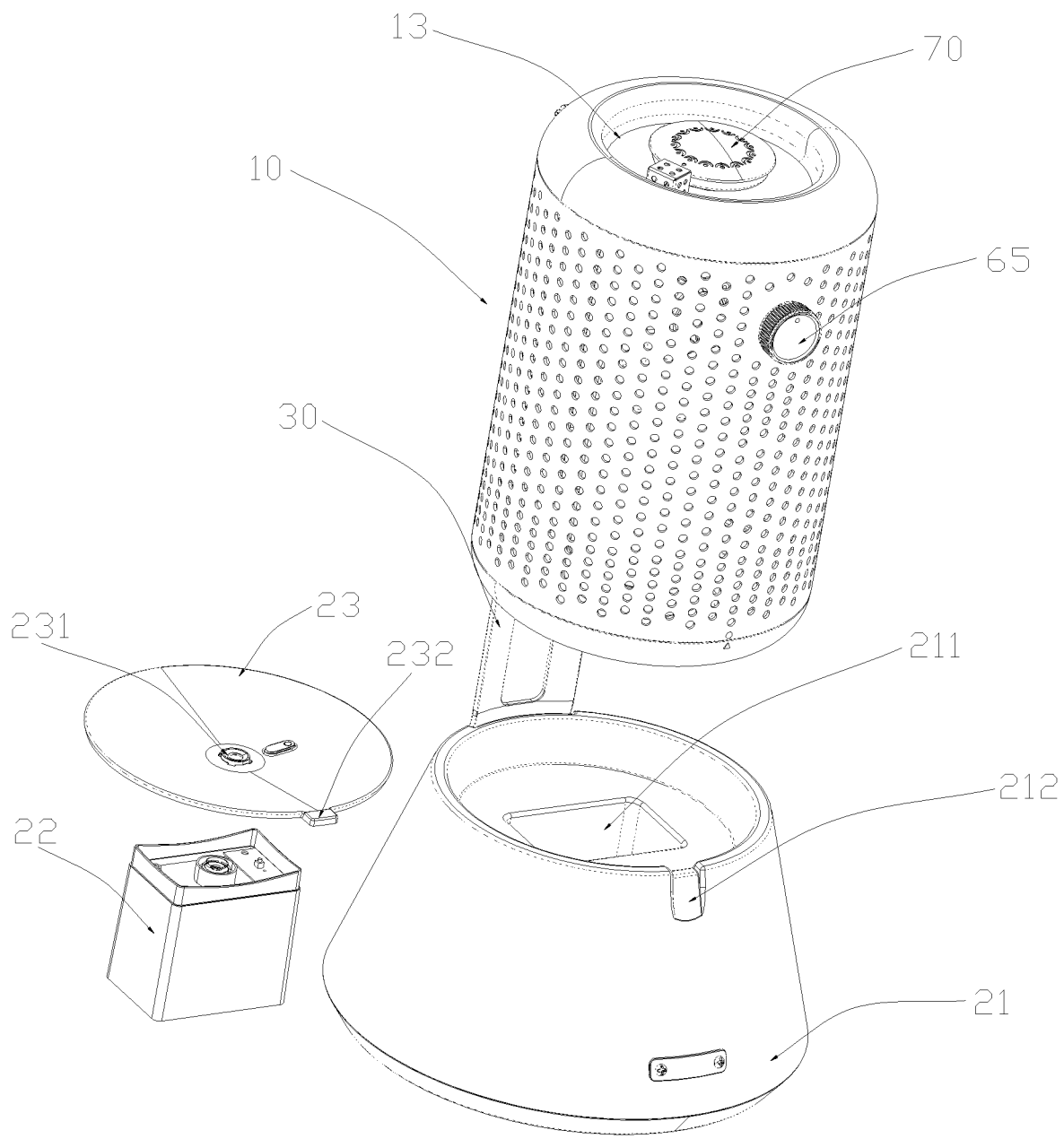
FIG. 9 is a schematic diagram of the explosion structure of a stove according to the present disclosure.

Referring to FIGS. 1 to 9, a stove with a mosquito repellent component includes:

a stove component 10, wherein the stove component 10 is configured to contain fuel and allow the fuel to burn;

a mosquito repellent component 20, wherein the mosquito repellent component 20 is provided below the stove component 10, the mosquito repellent component 20 is configured to atomize mosquito repellent liquid to generate rising mosquito repellent smoke, and the bottom of the stove component 10 blocks the mosquito repellent smoke and causes the mosquito repellent smoke to spread around along the bottom surface of the stove component 10.

Through the arrangement of the above structure, when in use, the stove component contains fuel and allows the fuel to burn, so that users can use the stove component for heating, lighting and cooking. A mosquito repellent component atomizes mosquito repellent liquid. Mosquito repellent smoke drifts upward. When meeting the bottom of the stove component, the smoke spreads around along the bottom surface of the stove component, so that the mosquito repellent smoke effectively diffuses around the stove, thereby effectively killing and driving mosquitoes around the stove and protecting users around the stove. The stove is simple in structure, convenient to use and excellent in mosquito repellent effect.

In this embodiment, the stove further includes a support arm 30. The lower end of the support arm 30 is connected to the mosquito repellent component 20. The upper end of the support arm 30 is connected to the stove component 10. A rising space 40 is formed between the bottom of the stove component 10 and the upper part of the mosquito repellent component 20. The rising space 40 is configured to allow mosquito repellent smoke to rise and to be used. Through the arrangement of the above structure, both ends of the support arm are connected with the stove component and the mosquito repellent component, respectively, so that the stove component and the mosquito repellent component are effectively connected. A smoke rising space is formed between the stove component and the mosquito repellent component. The mosquito repellent smoke generated by the mosquito repellent component rises and spreads in the rising space, and the volume of the mosquito repellent smoke becomes larger. At this time, the smoke touches the bottom of the stove component again, and it is easier to spread around along the bottom of the stove component, thereby improving the mosquito repellent effect. Moreover, the arrangement of the support arm also improves the height of the stove component, which is convenient for users to use.

In this embodiment, the top of the support arm 30 is provided with a shaft hole 31. The top of the stove component 10 is provided with a rotating shaft 11. The rotating shaft 11 is rotatably connected to the shaft hole 31. When the stove component 10 is in working state, the stove component 10 abuts against the support arm 30. Through the arrangement of the above structure, the shaft hole on the support arm matches the rotating shaft on the stove component, so that the stove component can be rotatably connected with the support arm, and users can adjust and clean the stove component conveniently. For example, users can rotate the stove component to replenish fuel or clean at a proper position, which is convenient for users to use.

In this embodiment, one side of the support arm 30 facing the stove component 10 is provided with an abutting surface 34. When the stove component 10 is in working state, the stove component 10 abuts against the abutting surface 34, and the shape of the abutting surface 34 matches the shape of the outer surface of the stove component 10. Through the arrangement of the above structure, when the stove component is in working state, at this time, the stove component rotates downwards under the action of gravity. The stove component abuts against the abutting surface, and the shape of the abutting surface matches the shape of the outer surface of the stove component, so that the contact area between the stove component and the abutting surface can be increased, and the stability of the product can be improved.

In this embodiment, the stove component 10 is provided with a locking member 14. The locking member rotatably protrudes from the surface of the stove component 10. The surface of the support arm 30 is provided with a limiting hole 35. The shape of the limiting hole 35 matches the shape of the locking member 14. When the locking member 14 rotates to the unlocking position, the locking member 14 penetrates into the limiting hole 35; and when the locking member 14 rotates to the locking position, the locking member 14 abuts against the surface of the support arm 30. Through the arrangement of the above structure, the locking member is rotated to the unlocking position. At this time, because the shape of the limiting hole matches the shape of the locking member, the stove component can rotate with respect to the supporting arm, and the locking member can penetrate into or out of the limiting hole. When the stove component is in working state and the stove component rotates downwards to the working position under the action of gravity, the locking member penetrates into the limiting hole, and the locking member rotates to the locking position. At this time, the locking member abuts against the surface of the support arm to block the relative rotation between the stove component and the support arm, so that the structure is simple and it is convenient to use.

In this embodiment, the stove further includes a fuel tank 50. An accommodating space 12 is provided in the stove component 10, and the fuel tank 50 is detachably provided in the accommodating space 12. Through the arrangement of the above structure, the fuel tank is placed in the accommodating space, so that the fuel tank can be effectively protected and hidden. On the one hand, the aesthetics of products can be improved, and on the other hand, the fuel tank can be prevented from being hit, and the safety of products and users can be effectively protected. Moreover, the fuel tank is detachably provided, which is also convenient for users to replace the fuel tank. When in use, the stove component can be rotated and the position of the stove component can be adjusted, which further facilitates users to replace the fuel tank, improves the endurance of products, and improves the user experience.

In this embodiment, the stove component 10 includes a bottom cover 15, and the bottom cover 15 is detachably connected to the bottom of the stove component 10 and covers the accommodating space 12. Through the arrangement of the structure, when in use, the stove component is rotated. The position of the stove component is adjusted, and the bottom cover is removed, so that users can conveniently open the accommodating space and disassemble the fuel tank, which is convenient for users to replace the fuel tank and is convenient for users to use.

In this embodiment, the stove further includes a gas stove component 60. The gas stove component 60 is provided in the accommodating space 12. The gas stove component 60 is provided with a gas inlet 61, and the gas inlet 61 is communicated with the tank opening 51 of the fuel tank 50. Through the arrangement of the above structure, when in use, the fuel tank is connected to the gas stove component. At this time, the tank opening of the fuel tank is communicated with the gas inlet, so that the combustible gas in the fuel tank can flow into the gas stove component, thereby effectively burning. It is convenient for users to carry out lighting, heating and cooking.

In this embodiment, the gas stove component 60 is provided with a gas guide channel 62. The gas inlet 61 is provided at one end of the gas guide channel 62, and the other end of the gas guide channel 62 is provided with a gas outlet 63. The gas outlet 63 penetrates out of the accommodating space 12. Through the arrangement of the above structure, when in use, the combustible gas in the fuel tank flows into the gas inlet from the tank opening and flows out along the gas outlet through the gas guide channel. The gas outlet penetrates out of the accommodating space, so that the fuel gas can be burned outside the accommodating space.

In this embodiment, the gas stove component 60 is provided with a pressure reducing valve 64, and the pressure reducing valve 64 is communicated with the gas guide channel 62. Through the arrangement of the above structure, the pressure reducing valve is provided, which can adjust and reduce the output pressure of the combustible gas in the gas guide channel. In this way, the combustible gas can stably and continuously flow out along the gas guide channel, ensuring that the flame of the stove component is stable. Moreover, reducing the pressure of the combustible gas can make the combustible gas fully burn, avoiding the insufficient combustion due to the excessive flow rate of the combustible gas, effectively saving energy and protecting the environment.

In this embodiment, the stove further includes a fire distributor 70. The fire distributor 70 is provided at the top of the stove component 10. The surface of the fire distributor 70 is provided with a fire outlet 71, and the fire outlet 71 is communicated with the gas outlet 63. Through the arrangement of the above structure, the fire distributor is provided at the top of the stove component. When in use, combustible gas flows out from the gas outlet and burns. The flame escapes from each fire outlet. A stable and continuous flame can be provided at the top of the stove component, which is convenient for users to carry out heating, cooking and lighting.

In this embodiment, the top of the stove component 10 is provided with an accommodating groove 13 which is sunken downwards. The fire distributor 70 is provided in the accommodating groove 13, and the depth of the accommodating groove 13 matches the height of the fire distributor 70. Through the arrangement of the structure, when in use, the fire distributor is provided in the accommodating groove, which can effectively protect the fire distributor, prevent the fire distributor from being damaged and prolong the service life of the product. In addition, the depth of the accommodating groove matches the height of the fire distributor, so that the windproof effect can be achieved, the flame can be continuously stabilized, the flame can be prevented from being extinguished accidentally, and the stability of the product can be improved.

In this embodiment, the stove further includes an adjusting knob 65. The gas stove component 60 is further provided with an adjusting device 66. The adjusting device 66 is configured to adjust the flow rate of combustible gas flowing through the gas guide channel 62. The adjusting rod of the adjusting knob 65 is connected to the adjusting device 66 through the side wall of the stove component 10, and the adjusting knob 65 is configured to adjust the adjusting device 66. Through the arrangement of the structure, when in use, the adjusting knob is screwed to drive the adjusting device, so that the gas guide channel can be turned on or off to control the ignition or extinction of the flame. At the same time, the flame size is controlled by adjusting the flow rate of combustible gas. Users can adjust the flame according to their demands, and the use experience of users is improved. The adjusting knob is provided on the outer side of the side wall of the stove component 1, which is convenient for users to adjust and is excellent in use effect.

In this embodiment, the mosquito repellent component 20 includes a shell 21, an ultrasonic atomizer 22 and a cover 23. The upper surface of the shell 21 is sunken downwards to form an installation groove 211. The ultrasonic atomizer 22 is detachably provided in the installation groove 211. The cover 23 is provided with a smoke outlet 231. The cover 23 covers the installation groove 211. The smoke outlet 231 corresponds to the ultrasonic atomizer 22. Through the arrangement of the structure, when in use, the ultrasonic atomizer is installed in the installation groove, so that the ultrasonic atomizer can be effectively fixed and accommodated, and the ultrasonic atomizer can be conveniently replaced and maintained by users. The cover covers the installation groove, which can further protect the ultrasonic atomizer and prevent the ultrasonic atomizer from being damaged. When the cover covers the installation groove, the ultrasonic atomizer corresponds to the smoke outlet, and the mosquito repellent smoke atomized by the ultrasonic atomizer can flow out along the smoke outlet.

In this embodiment, the ultrasonic atomizer 22 includes an ultrasonic atomizing module 221, a sponge rod 222 and a mosquito repellent liquid container 223. The mosquito repellent liquid container 223 is configured to contain mosquito repellent liquid. The ultrasonic atomizing module 221 is provided at the bottle opening of the mosquito repellent liquid container 223. The sponge rod 222 is connected to the ultrasonic atomizing module 221. The sponge rod 222 is inserted into the mosquito repellent liquid container 223, and at least part of the sponge rod 222 is immersed in the mosquito repellent liquid. Through the arrangement of the structure, when in use, the sponge rod is inserted into the mosquito repellent container. The sponge rod absorbs mosquito repellent liquid and guides the mosquito repellent liquid into the ultrasonic atomizing module. The ultrasonic atomizing module atomizes the mosquito repellent liquid to generate mosquito repellent smoke. The mosquito repellent liquid can be continuously and stably guided into the ultrasonic atomizing module, thus effectively ensuring the mosquito repellent effect of the product.

In this embodiment, the ultrasonic atomizer 22 further includes a battery 224, and the battery 224 is electrically connected to the ultrasonic atomizing module 221. Through the arrangement of the above structure, the battery can continuously supply power to the ultrasonic atomizing module and provide energy, and users can easily replace the battery, thus improving the endurance of the product.

In this embodiment, the surface of the shell 21 is provided with a slot 212. A hand-held part 232 protrudes from the edge of the cover 23. When the cover 23 covers the installation groove 211, the hand-held part 232 is inserted into the slot 212. Through the arrangement of the above structure, when in use, users can slide their hands along the slot, which is convenient for users to grasp the hand-held part. Users can conveniently assemble and disassemble the cover, which is convenient for users to use.

In this embodiment, the mosquito repellent component 20 further includes a counterweight 24. The shell 21 is provided with an accommodating cavity 213. The counterweight 24 is provided at the bottom of the accommodating cavity 213. Through the arrangement of the above structure, the counterweight is provided at the bottom of the accommodating cavity, which can effectively reduce the center of gravity of the product, make the product more stable and improve the safety of the product.

One or more implementation modes are provided above in combination with specific contents, and it is not deemed that the specific implementation of the present disclosure is limited to these specifications. Any technical deductions or replacements approximate or similar to the method and structure of the present disclosure or made under the concept of the present disclosure shall fall within the scope of protection of the present disclosure.

What is claimed is:

1. A stove with a mosquito repellent component, comprising:
   a stove component, wherein the stove component is configured to contain fuel and allow the fuel to burn;
   a mosquito repellent component, wherein the mosquito repellent component is provided below the stove component, the mosquito repellent component is configured to atomize mosquito repellent liquid to generate rising mosquito repellent smoke, and the bottom of the stove component blocks the mosquito repellent smoke and causes the mosquito repellent smoke to spread around along the bottom surface of the stove component;
   wherein the stove with a mosquito repellent component further comprising a support arm, wherein the lower end of the support arm is connected to the mosquito repellent component, the upper end of the support arm is connected to the stove component, a rising space is formed between the bottom of the stove component and the upper part of the mosquito repellent component, and the rising space is configured to allow mosquito repellent smoke to rise and to be used;
   wherein the top of the support arm is provided with a shaft hole, the top of the stove component is provided with a rotating shaft, the rotating shaft is rotatably connected to the shaft hole, and when the stove component is in working state, the stove component abuts against the support arm.

2. The stove with a mosquito repellent component according to claim 1, wherein the stove component is provided with a locking member, the locking member rotatably protrudes from the surface of the stove component, the surface of the support arm is provided with a limiting hole, the shape of the limiting hole matches the shape of the locking member, when the locking member rotates to the unlocking position, the locking member penetrates into the limiting hole; and when the locking member rotates to the locking position, the locking member abuts against the surface of the support arm.

3. The stove with a mosquito repellent component according to claim 2, further comprising a fuel tank, wherein an accommodating space is provided in the stove component, and the fuel tank is detachably provided in the accommodating space.

4. The stove with a mosquito repellent component according to claim 3, wherein the stove component comprises a bottom cover, and the bottom cover is detachably connected to the bottom of the stove component and covers the accommodating space.

5. The stove with a mosquito repellent component according to claim 1, wherein the mosquito repellent component comprises a shell, an ultrasonic atomizer and a cover, the upper surface of the shell is sunken downwards to form an installation groove, the ultrasonic atomizer is detachably provided in the installation groove, the cover is provided with a smoke outlet, the cover covers the installation groove, and the smoke outlet corresponds to the ultrasonic atomizer.

6. The stove with a mosquito repellent component according to claim 5, wherein the ultrasonic atomizer comprises an ultrasonic atomizing module, a sponge rod and a mosquito repellent liquid container, the mosquito repellent liquid container is configured to contain mosquito repellent liquid, the ultrasonic atomizing module is provided at the bottle opening of the mosquito repellent liquid container, the sponge rod is connected to the ultrasonic atomizing module, the sponge rod is inserted into the mosquito repellent liquid container, and at least part of the sponge rod is immersed in the mosquito repellent liquid.

7. The stove with a mosquito repellent component according to claim 6, wherein the surface of the shell is provided with a slot, a hand-held part protrudes from the edge of the cover, and when the cover covers the installation groove, the hand-held part is inserted into the slot.

8. The stove with a mosquito repellent component according to claim 7, wherein the mosquito repellent component further comprises a counterweight, the shell is provided with an accommodating cavity, and the counterweight is provided at the bottom of the accommodating cavity.

9. A stove with a mosquito repellent component, comprising:
   a stove component configured to contain fuel and allow the fuel to burn;
   a mosquito repellent component is provided below the stove component, the mosquito repellent component configured to atomize mosquito repellent liquid to generate rising mosquito repellent smoke, and a bottom surface of the stove component configured to block the mosquito repellent smoke and causes the mosquito repellent smoke to spread around along the bottom surface of the stove component;
   wherein the mosquito repellent component comprises a shell, an ultrasonic atomizer and a cover, the upper surface of the shell is sunken downwards to form an installation groove, the ultrasonic atomizer is detachably provided in the installation groove, the cover is provided with a smoke outlet, the cover covers the installation groove, and the smoke outlet corresponds to the ultrasonic atomizer.

10. The stove with a mosquito repellent component according to claim 9, further comprising a support arm, wherein the lower end of the support arm is connected to the mosquito repellent component, the upper end of the support arm is connected to the stove component, a rising space is formed between the bottom surface of the stove component and the upper part of the mosquito repellent component, and the rising space is configured to allow mosquito repellent smoke to rise and to be used.

11. The stove with a mosquito repellent component according to claim 10, wherein the top of the support arm is provided with a shaft hole, the top of the stove component is provided with a rotating shaft, the rotating shaft is rotatably connected to the shaft hole, and when the stove component is in working state, the stove component abuts against the support arm.

12. The stove with a mosquito repellent component according to claim 11, wherein the stove component is provided with a locking member, the locking member rotatably protrudes from the surface of the stove component, the surface of the support arm is provided with a limiting hole, the shape of the limiting hole matches the shape of the locking member, when the locking member rotates to the unlocking position, the locking member penetrates into the limiting hole; and when the locking member rotates to the locking position, the locking member abuts against the surface of the support arm.

13. The stove with a mosquito repellent component according to claim 12, further comprising a fuel tank, wherein an accommodating space is provided in the stove component, and the fuel tank is detachably provided in the accommodating space.

14. The stove with a mosquito repellent component according to claim 13, wherein the stove component comprises a bottom cover, and the bottom cover is detachably connected to the stove component and covers the accommodating space.

15. The stove with a mosquito repellent component according to claim 9, wherein the ultrasonic atomizer comprises an ultrasonic atomizing module, a sponge rod and a mosquito repellent liquid container, the mosquito repellent liquid container is configured to contain mosquito repellent liquid, the ultrasonic atomizing module is provided at the bottle opening of the mosquito repellent liquid container, the sponge rod is connected to the ultrasonic atomizing module, the sponge rod is inserted into the mosquito repellent liquid container, and at least part of the sponge rod is immersed in the mosquito repellent liquid.

16. The stove with a mosquito repellent component according to claim 15, wherein the surface of the shell is provided with a slot, a hand-held part protrudes from the edge of the cover, and when the cover covers the installation groove, the hand-held part is inserted into the slot.

17. The stove with a mosquito repellent component according to claim 16, wherein the mosquito repellent component further comprises a counterweight, the shell is provided with an accommodating cavity, and the counterweight is provided at the accommodating cavity.

* * * * *